(12) United States Patent
Kim

(10) Patent No.: US 7,393,210 B2
(45) Date of Patent: Jul. 1, 2008

(54) DENTAL IMPLANT DEVICE AND CORRECTION DEVICE THEREFOR

(76) Inventor: Man Yong Kim, #8-301 Jinheung Apt., 1315, Seocho-dong, Seocho-gu, Seoul 137-070 (KR)

( * ) Notice: Subject to any disclaimer, the term of this patent is extended or adjusted under 35 U.S.C. 154(b) by 0 days.

(21) Appl. No.: 11/231,277

(22) Filed: Sep. 20, 2005

(65) Prior Publication Data
US 2007/0054241 A1    Mar. 8, 2007

(30) Foreign Application Priority Data
Sep. 5, 2005    (KR) .............. 10-2005-0038335

(51) Int. Cl.
*A61C 8/00*    (2006.01)
(52) U.S. Cl. ............................................. 433/173
(58) Field of Classification Search .......... 433/172–176
See application file for complete search history.

(56) References Cited

U.S. PATENT DOCUMENTS

| | | | | |
|---|---|---|---|---|
| 5,213,502 A | * | 5/1993 | Daftary | 433/172 |
| 5,344,457 A | * | 9/1994 | Pilliar et al. | 606/60 |
| 5,733,124 A | * | 3/1998 | Kwan | 433/173 |
| 5,882,200 A | * | 3/1999 | Sutter et al. | 433/173 |
| 6,068,478 A | * | 5/2000 | Grande et al. | 433/172 |
| 2004/0076924 A1 | * | 4/2004 | Kim | 433/173 |

* cited by examiner

*Primary Examiner*—John J Wilson
(74) *Attorney, Agent, or Firm*—Bachman & LaPointe, P.C.

(57) ABSTRACT

The present invention relates to a dental implant device. A fixture is provided with an abutment coupler at the upper portion of a commercialized fixture type. The abutment coupler has a female screw formed inside, and is formed at the lower portion with an implant screw. An abutment is formed at the lower portion with a first coupler and at the upper portion with a second coupler. The first coupler is coupled to the abutment coupler, and provided with a first sleeve resting groove on the outer circumferential surface of the second coupler. A solid screw is formed at the lower portion with a coupling screw and at the upper portion with a head. The head has a second sleeve resting groove formed on the outer circumferential surface thereof, in which sleeves formed inside an artificial tooth crown are press-fittingly coupled to the first and the second sleeve resting grooves.

5 Claims, 18 Drawing Sheets

(PRIOR ART)

(PRIOR ART)

(PRIOR ART)

(PRIOR ART)

DENTAL IMPLANT DEVICE AND CORRECTION DEVICE THEREFOR

BACKGROUND OF THE INVENTION

1. Field of the Invention

The present invention relates to a dental implant device and a correction device therefor. More specifically, the invention relates to a dental implant device, in which the sleeve of an artificial tooth crown is coupled to the sleeve resting grooves formed on the outer circumferential surfaces of an abutment and a solid screw, the abutment and the solid screw coupled to a fixture implanted into an edentulous site of a jawbone, so that a screw-loosening problem can be prevented. The invention also relates to a correction device used for the dental implant device, which allows the exact locations of the abutment and the solid screw in an oral cavity to be transferred to a working model.

2. Background of the Related Art

In general, a dental implant is a substitute itself for a lost natural tooth, or a dental operation, in which a screw shape fixture is secured to the jawbone and fused with the jawbone for a predetermined period of time, and then an abutment, i.e. a coupling part, and a prosthesis such as an artificial tooth crown are fixed to the fixture so as to restore the original function of a tooth.

An example of the dental implant described above is "Dental Implant Structure", Korean Patent Application No. 2002-0027055, filed by the present inventor.

FIG. 1 shows a structure of a conventional dental implant.

As shown in FIG. 1, the dental implant comprises: a fixture 1 having a screw coupling hole 1a formed at the inside thereof along the central axis thereof by a predetermined depth, the fixture being opened at the upper end thereof, and a threaded screw 1b formed on the outer circumferential surface thereof; an abutment 2 coupled to the upper end of the fixture 1 and having a locking slit 2a formed at the upper portion of the outer circumferential surface thereof; a screw 3 coupled to the screw coupling hole 1a of the fixture 1 through the abutment 2 and having a sleeve inserting groove 3a formed at the upper portion thereof to be connected to the locking slit 2a of the abutment 2; and a locking sleeve 4 or a general screw 3b, the sleeve fitted into both the locking slit 2a of the abutment 2 and the sleeve inserting groove 3a of the screw 3.

In addition, a coupling part 1c of a polygonal shape is formed at the upper end of the fixture 1 and a corresponding recess part 2b is formed at the lower end of the abutment 2, such that the coupling part 1c and the recess part 2b are coupled to each other, thereby preventing rotation of the abutment 2 when the abutment 2 is coupled to the fixture 1.

In addition, an artificial tooth crown coupled to the outside of the abutment 2 is set up through the following steps which are not described in the conventional application.

FIGS. 2 to 6 show a conventional operation process of a dental implant.

First, the fixture 1 is implanted into an edentulous site of a jawbone and firmly coupled to the jawbone in 6 months or so if the jawbone is in the upper jaw, whereas 4 months or so are required if it is in the lower jaw. (refer to FIG. 2)

With the fixture 1 being firmly fixed as above, a dental analog 5 is coupled to the fixture 1 and an impression 6 is taken. (refer to FIG. 3)

With the impression 6 being taken, a wrap analog 7 is coupled to the dental analog 5 which is embedded in the impression 6, and with a silicon 8 of a gum shape being coupled to the impression 6, a working model 9 is formed by filling plaster. (refer to FIG. 4)

With the working model 9 being formed as above, the impression 6 is separated, and the work is performed with the crown 10 being fixed to the working model 9.

At this point, with the abutment and the screw being coupled to the wrap analog 7 which is fitted into the working model 9, the crown 10 is coupled. (refer to FIG. 5)

Then, with the abutment 2, the screw 3, and the locking sleeve 4 being coupled to the fixture 1 inside an oral cavity, the crown 10 is fixed to the outside of the abutment 2. At this point, cement is used to bond the abutment 2 and the crown 10. (refer to FIG. 6)

However, a conventional implant structure has problems described below.

First, in a conventional operation procedure using a screw, the crown 10 cannot be free from the screw-loosening problem.

Second, since the a thread of the conventional implant fixture 1 is connected to an inner screw, due to the mechanical tolerance between the thread of the fixture 1 and the dental analog 5, the tolerance made during the process of transferring to the working model 9, the crown 10 manufactured at the working model 9 does not fit inside the oral cavity.

Third, conventionally, since the abutment 2 and the crown 10 are bonded by cement, when the screw comes loose, the crown 10 must be broken to tighten the screw again, and, furthermore, the screw-loosening problem occurs again.

SUMMARY OF THE INVENTION

Therefore, the present invention has been made in view of the above problems occurring in the prior art, and it is an object of the present invention to provide a dental implant device, in which the sleeve of an artificial tooth crown is coupled to the sleeve resting grooves formed on the outer circumferential surfaces of an abutment and a solid screw, the abutment and the solid screw coupled to a fixture implanted into an edentulous site of a jawbone, so that a screw-loosening problem can be prevented.

Another object of the invention is to provide a correction device used for the dental implant device, which allows the exact locations of the abutment and the solid screw inside an oral cavity to be transferred to a working model.

A further object of the invention is to provide a correction device used for the dental implant device, in which the solid head type screw and the abutment are assembled together with a dental analog body and the male screw of the solid screw is coupled to the female screw of an analog screw, thereby removing the rotational tolerance of the screw.

To accomplish the above objects, according to the present invention, there is provided a dental implant device. The device comprises: a fixture provided with an abutment coupler at the upper portion of a commercialized fixture type, the abutment coupler having a female screw formed inside, and formed at the lower portion with an implant screw inserted into the edentulous site of a jawbone; an abutment formed at the lower portion with a first coupler and at the upper portion with a second coupler, the first coupler being coupled to the abutment coupler, and provided with a first sleeve resting groove on the outer circumferential surface of the second coupler; and a solid screw formed at the lower portion with a coupling screw and at the upper portion with a head, the coupling screw passing through the abutment and coupled to the female screw of the fixture, the head having a second sleeve resting groove formed on the outer circumferential surface thereof to fluid-communicate with the first sleeve resting groove, in which sleeves formed inside an artificial tooth crown are press-fittingly coupled to the first and the second sleeve resting grooves.

In addition, the first and the second sleeve resting grooves are formed in at least two or more pieces.

In addition, the abutment coupler of the fixture and the corresponding first coupler of the abutment is formed in any one of rectangular, hexagonal and octagonal shapes.

In addition, an intermediate step is formed between the head and coupling screw of the solid screw so as to be tightly coupled to another step formed inside the second coupler of the abutment.

In addition, the height and/or width of the first and the second sleeve resting grooves are formed differently in size.

In addition, there is provided a correction device used for the dental implant device, the device comprising: a jig formed at the center of the upper portion with a receiving hole having a sleeve on the inner circumferential surface; a solid screw having a head and a coupling screw and being transferred to the receiving hole, the head formed with a second sleeve resting groove corresponding to the sleeve of the receiving hole, the coupling screw integrally formed at the other side of the head; an abutment penetratingly coupled to the coupling screw of the solid screw and formed with a first sleeve resting groove on the outer circumferential surface, the groove corresponding to the sleeve of the receiving hole; a dental analog body formed at the end portion with a coupler coupled to the abutment and at the center with a pass-through hole; and an analog screw formed at the inside with a female screw coupled to the dental analog body and the coupling screw of the solid screw at the same time.

In addition, the coupler of the analog body is formed in any one of rectangular, hexagonal and octagonal shapes.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

The preferred embodiments of the invention will be hereafter described in detail, with reference to the accompanying drawings. Hereafter, the operation for a damaged tooth in the lower jaw is explained as an example. However, it is not to be restricted by the example but can be applied to the upper jaw and to the case where a plurality of teeth is damaged.

Figure 1:
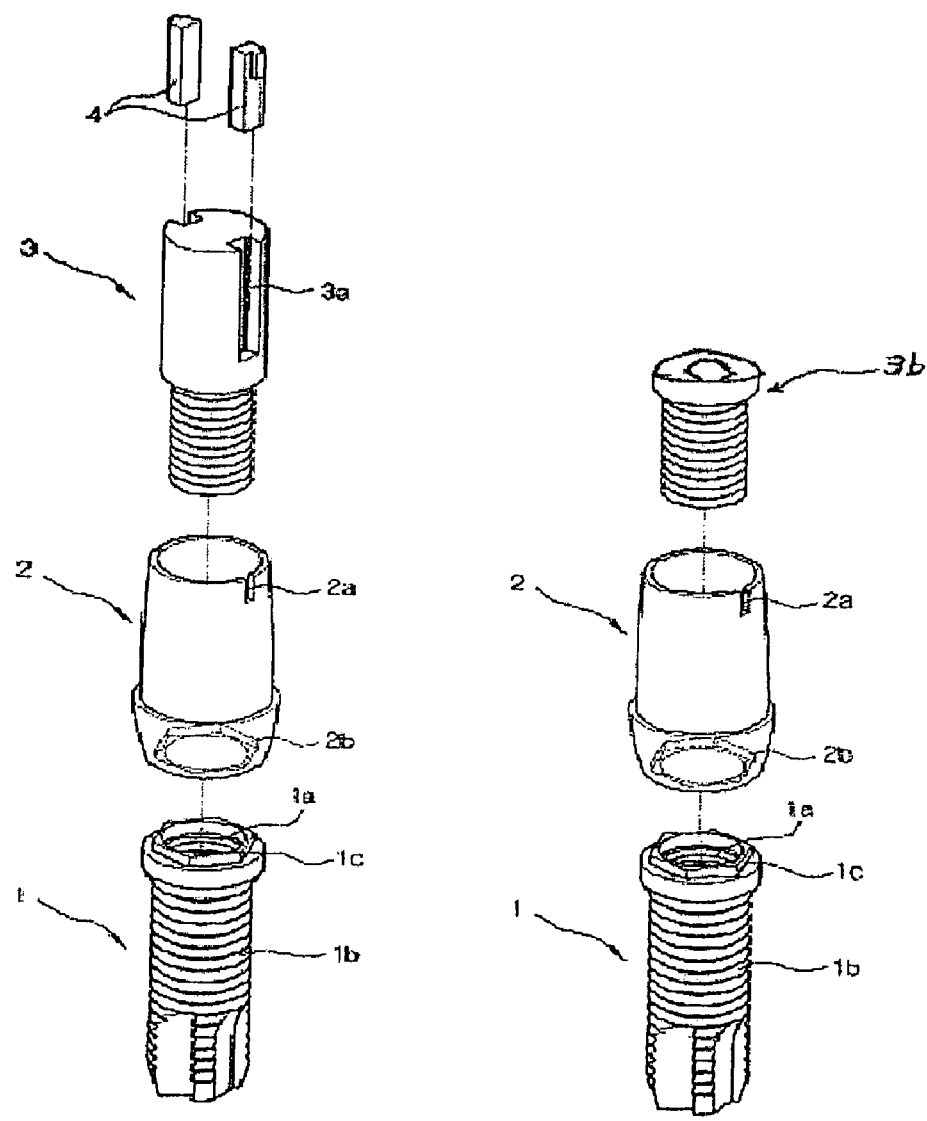
FIG. 1 shows a structure of a conventional dental implant.
Figure 2:
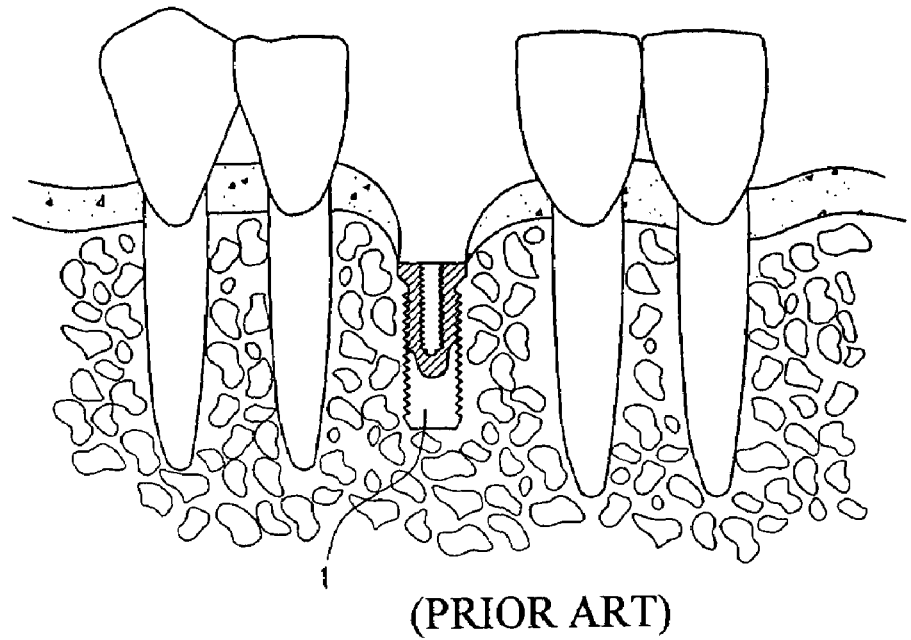
FIG. 2 shows an operation process of the conventional dental implant, in which a fixture fixed to a jawbone is shown.
Figure 3:
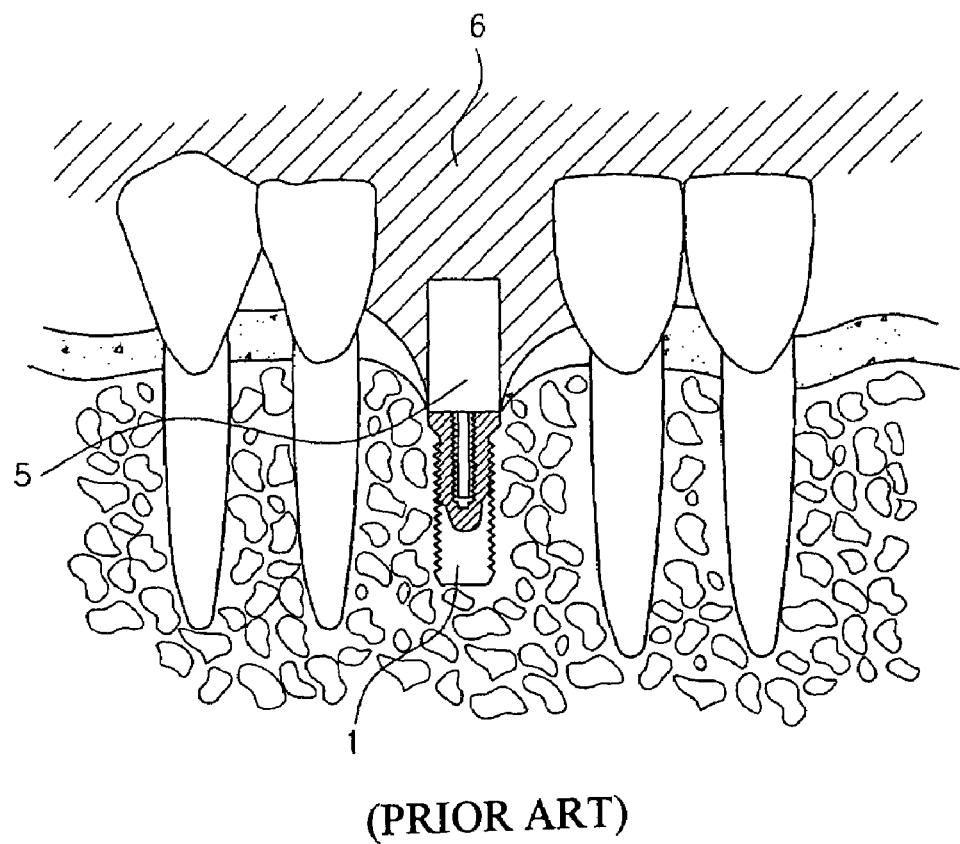
FIG. 3 shows the process of taking an impression in FIG. 2.
Figure 4:
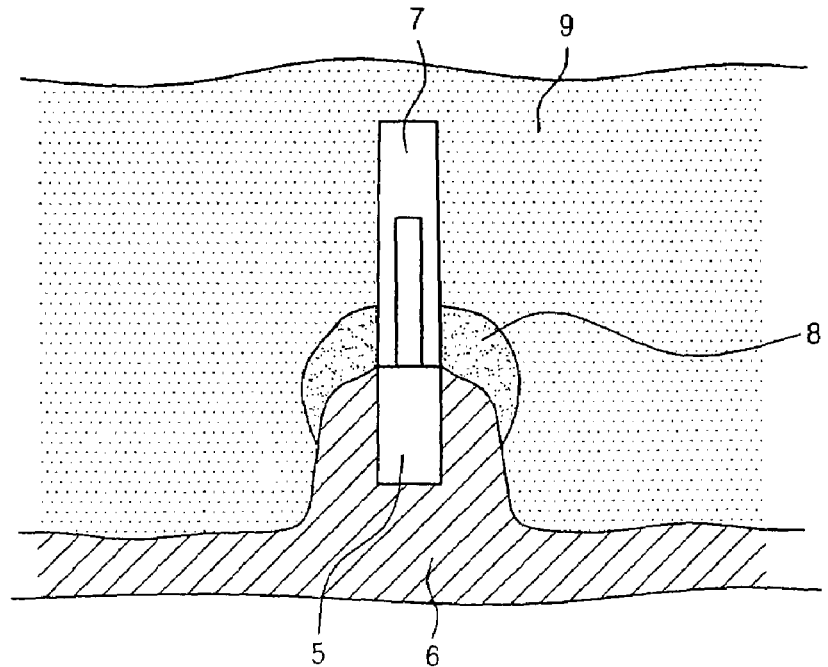
FIG. 4 shows the step of forming a working model by filling plaster in FIG. 3.
Figure 5:
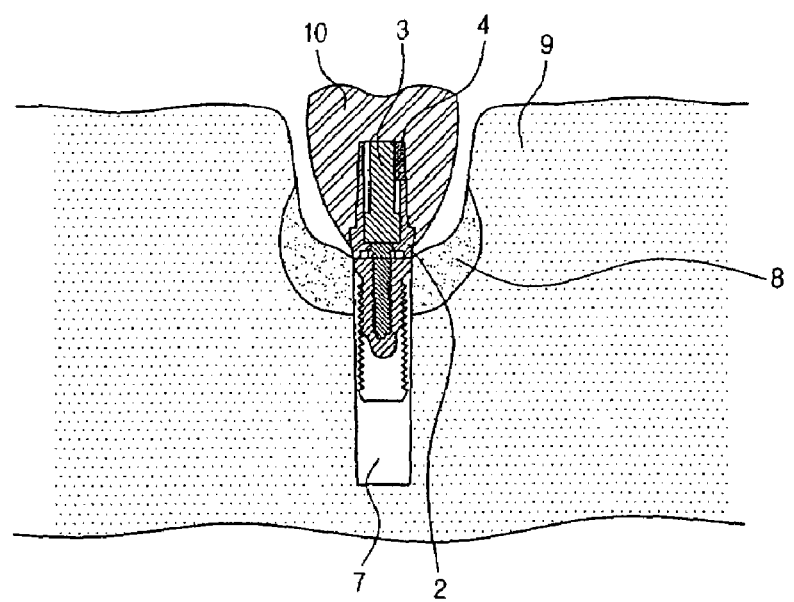
FIG. 5 shows the step of processing an artificial tooth crown at the working model of FIG. 4.
Figure 6:
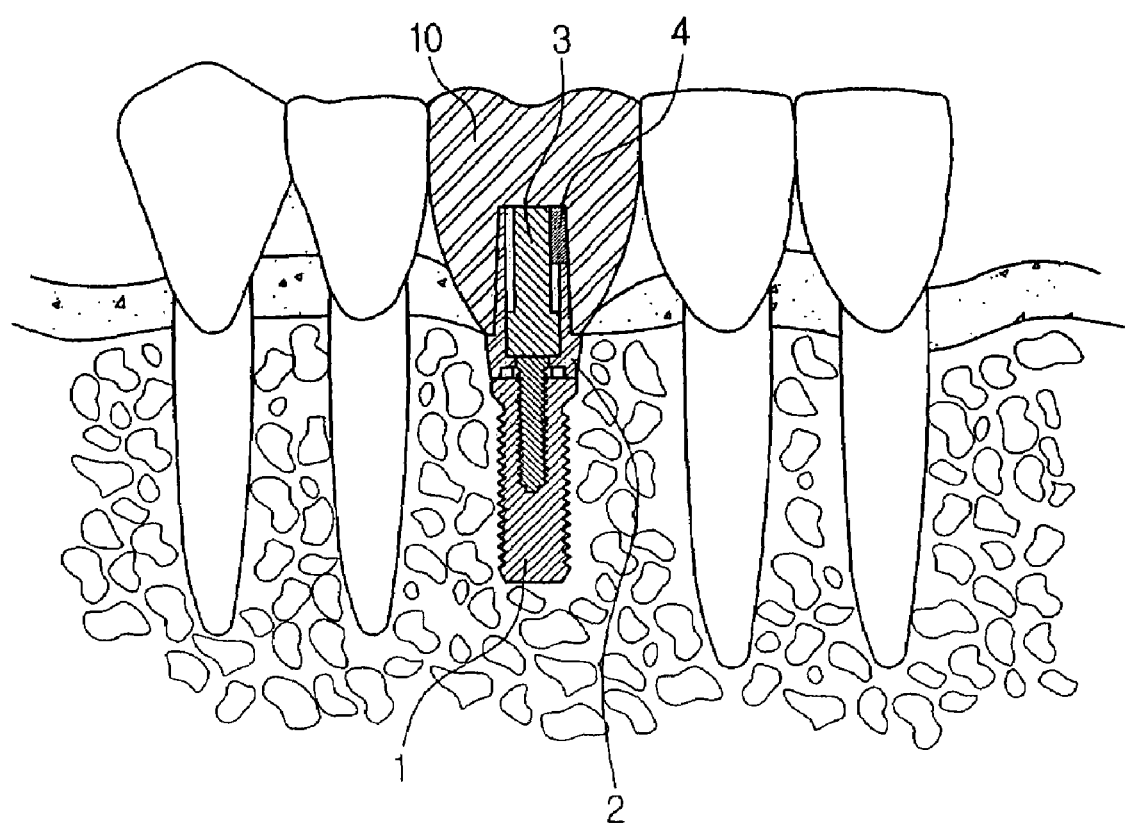
FIG. 6 shows a step of coupling the crown processed in FIG. 5 to the fixture in the oral cavity.
Figure 7:
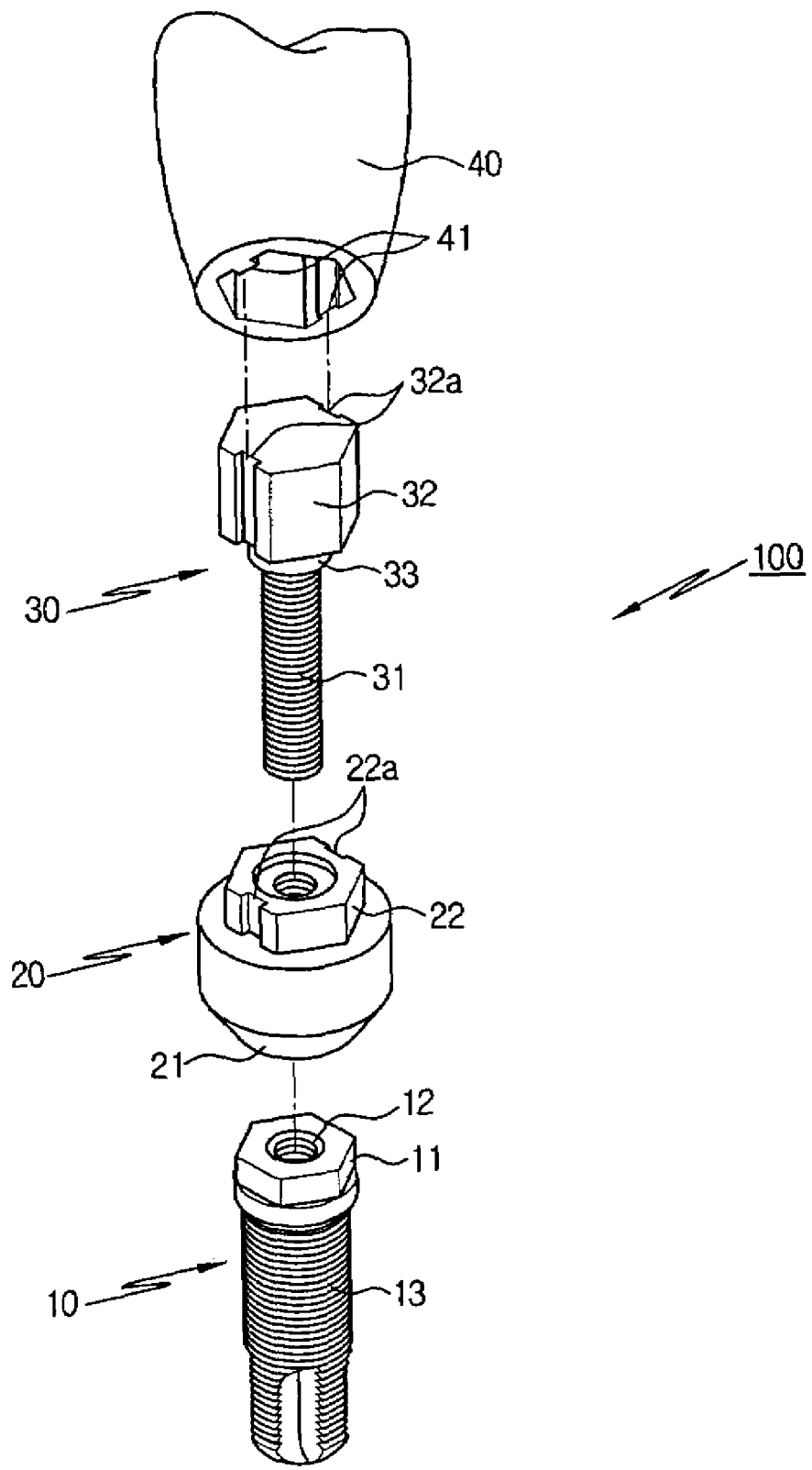
FIG. 7 is an exploded perspective view of a dental implant according to the present invention.
Figure 8:
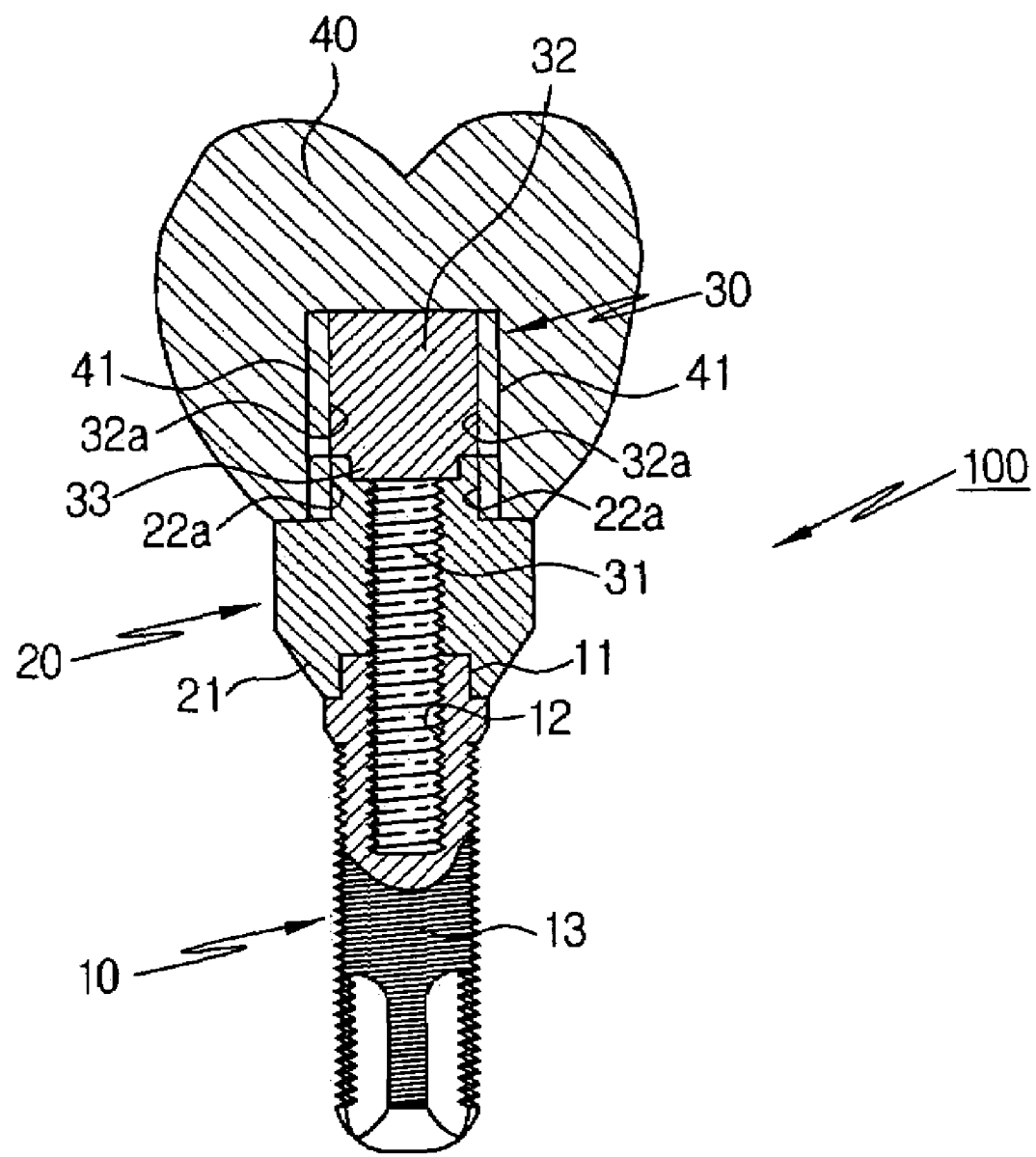
FIG. 8 is a cross-sectional view of an assembled dental implant according to the present invention.
Figure 9:
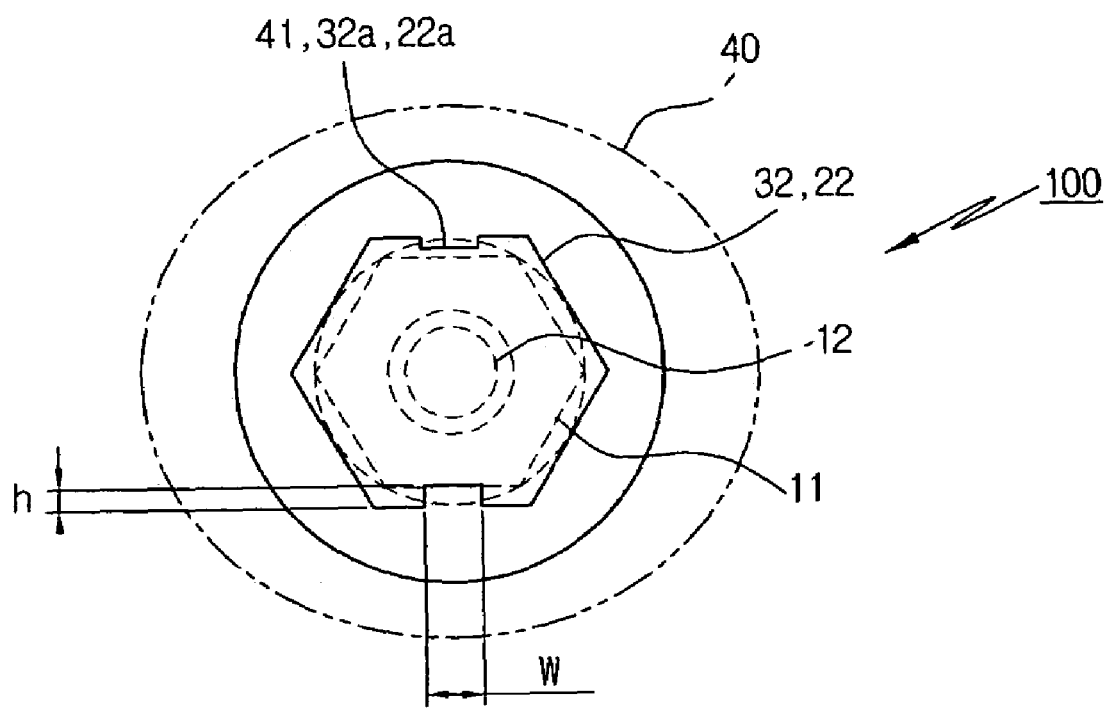
FIG. 9 is the dental implant viewed from above according to the present invention.

FIGS. 7 to 9 show a dental implant device according to the invention.

As shown in FIGS. 7 to 9, the dental implant device 100 of the invention comprises an implant fixture 10, an abutment 20, and a solid screw 30.

The fixture 10 is provided with an abutment coupler 11 at the upper portion, the abutment coupler 11 having a female screw thread 12 formed inside, and said fixture has a screw thread 13 formed at the lower portion for implanting the edentulous site of a jawbone.

The separate abutment 20 has at the lower portion thereof a first coupler 21 and at the upper portion thereof a second coupler 22, the first coupler 21 being coupled to the abutment coupler 11 of said fixture, and the abutment being provided with a first sleeve resting groove 22a on the outer circumferential surface of the second coupler 22.

In addition, the abutment coupler 11 of the fixture 10 and the corresponding first coupler 21 of the abutment 20 can be formed in any one of rectangular, hexagonal and octagonal shapes. A hexagonal shape is most preferable in order for a coupling tool to be used easily.

The solid screw 30 is formed at the lower portion with a coupling screw thread 31 and at the upper portion with a head 32. The coupling screw thread 31 passes through the abutment 20 and the coupling screw thread is coupled to the female screw thread 12 of the fixture 10, and the head 32 has a second sleeve resting groove 32a formed on the outer circumferential surface thereof to fluid-communicate with the first sleeve resting groove 22a. The first sleeve resting groove and the second sleeve resting groove are aligned.

In addition, an intermediate step 33 is formed between the head 32 and coupling screw thread 31 of the solid screw 30 so as to be tightly coupled to another step formed inside the second coupler 22 of the abutment 20.

In addition, a sleeve that is formed inside an artificial tooth and has a sleeve projection formed on the sleeve interior is press-fittingly coupled to the first and the second sleeve resting grooves 22*a*, 32*a*.

In addition, the first and the second sleeve resting grooves 22*a* 32*a* are formed in at least two or more pieces, preferably formed in two pieces at both sides symmetrically.

In addition, the height h and/or width w of the first and the second sleeve resting grooves 22*a* 32*a* are formed differently in size so that exact location can be found in the process of transfer described below.

Figure 10:
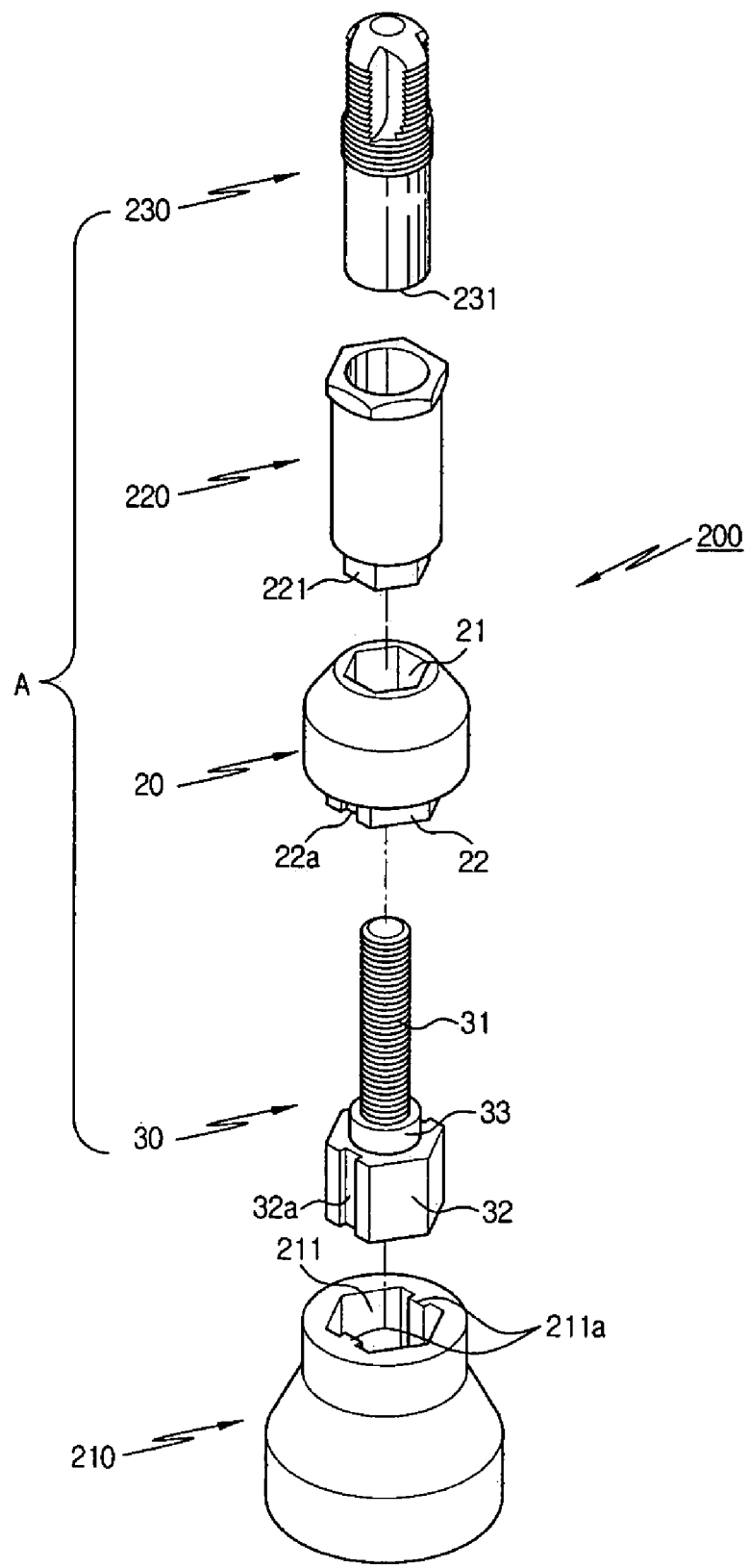
FIG. 10 is an exploded perspective view of a correction device used for the dental implant device according to the present invention.
Figure 11:
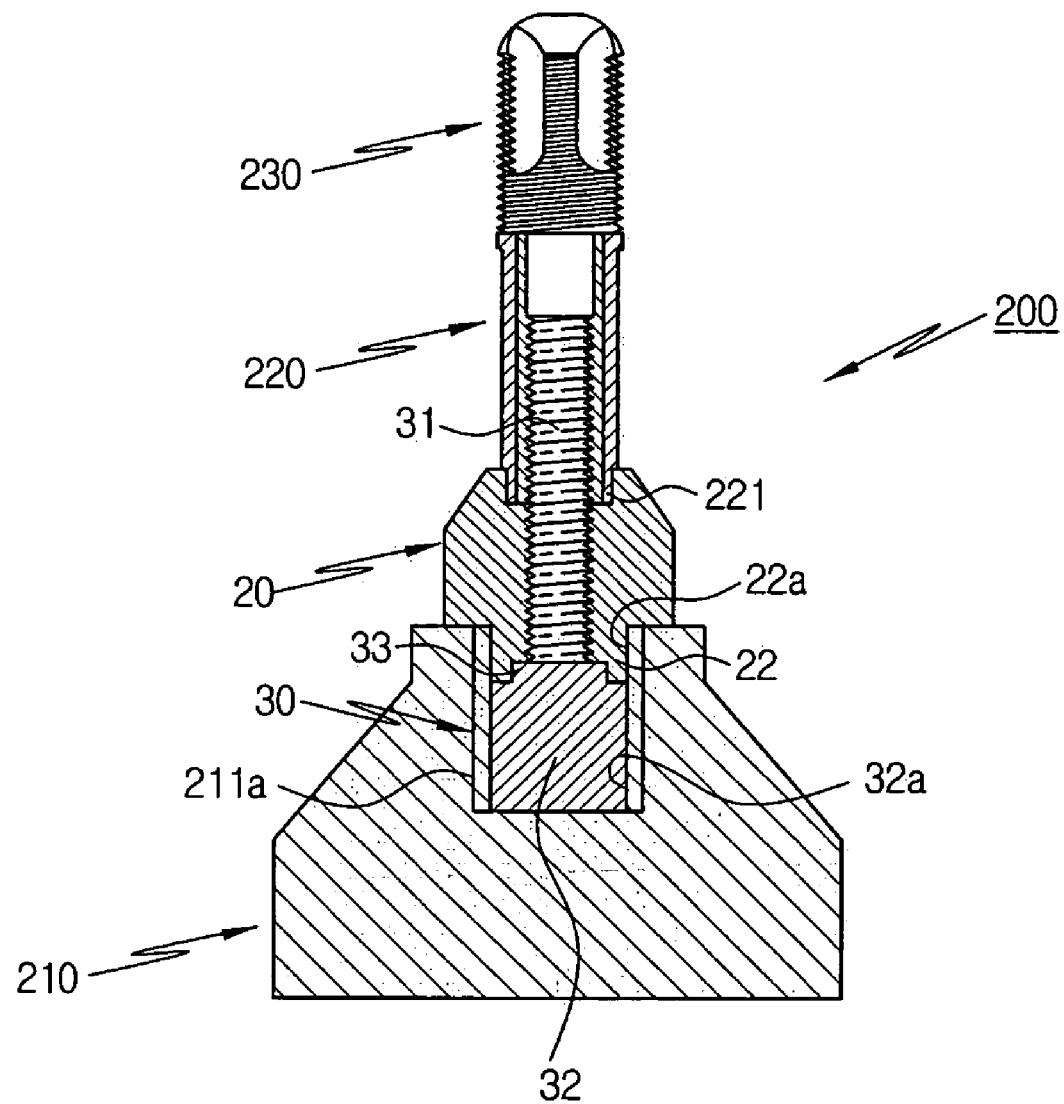
FIG. 11 is a cross-sectional view of an assembled correction device used for the dental implant device according to the present invention.

FIGS. 10 and 11 show a correction device used for the dental implant device according to the invention.

As shown in FIGS. 10 and 11, the correction device 200 used for the dental implant device comprises a jig 210, a solid screw 30, an abutment 20, a dental analog body 220, and an analog screw 230. For the convenience of explanation, the solid screw 30, the abutment 20, the dental analog body 220, and the analog screw 230 are integrally formed in one set, the set being referred to as an assembly A.

The jig 210 is formed at the center of the upper portion with a receiving hole 211, and a sleeve 211*a* is formed on the inner circumferential surface of the receiving hole 211.

Also, the sleeve 211*a* formed on the inner circumferential surface of the jig 210 corresponds to the first and the second sleeve resting grooves 22*a* 32*a* of the abutment 20 and the solid screw 30.

The solid screw 30 and the abutment 20 coupled to the fixture 10 are separated and coupled to the jig 210. The solid screw 30 having a head 32 and a coupling screw thread 31 is transferred to the receiving hole 211, the head 32 formed with the second sleeve resting groove 32*a* corresponding to the sleeve 211*a* of the receiving hole 211, the coupling screw thread 31 integrally formed at the other side of the head 32. The abutment 20 is penetratingly coupled to the coupling screw thread 31 of the solid screw 30 and formed with a first sleeve resting groove 22*a* on the outer circumferential surface, the groove corresponding to the sleeve 211*a* of the receiving hole 211.

The dental analog body 220 is formed at the end portion with a coupler 221 coupled to the abutment 20 and at the center with a pass-through hole.

In addition, the coupler 221 of the analog body 220 is formed in any one of rectangular, hexagonal and octagonal shapes. A hexagonal shape is most preferable in order to enhance the convenience of coupling.

The analog screw 230 is formed at one side with a female screw 231, the female screw coupled to the dental analog body 220 and the coupling screw thread 31 of the solid screw 30 at the same time.

That is, the female screw 231 of the analog screw 230 is fixed to the coupling screw thread 31 of the solid screw 30, and a correct transfer can be accomplished by the coupler 221 of the dental analog body 220 without having tolerance.

Hereafter, the process of an implant operation will be explained using the dental implant device and the correction device used thereof according to the invention.

Figure 12:
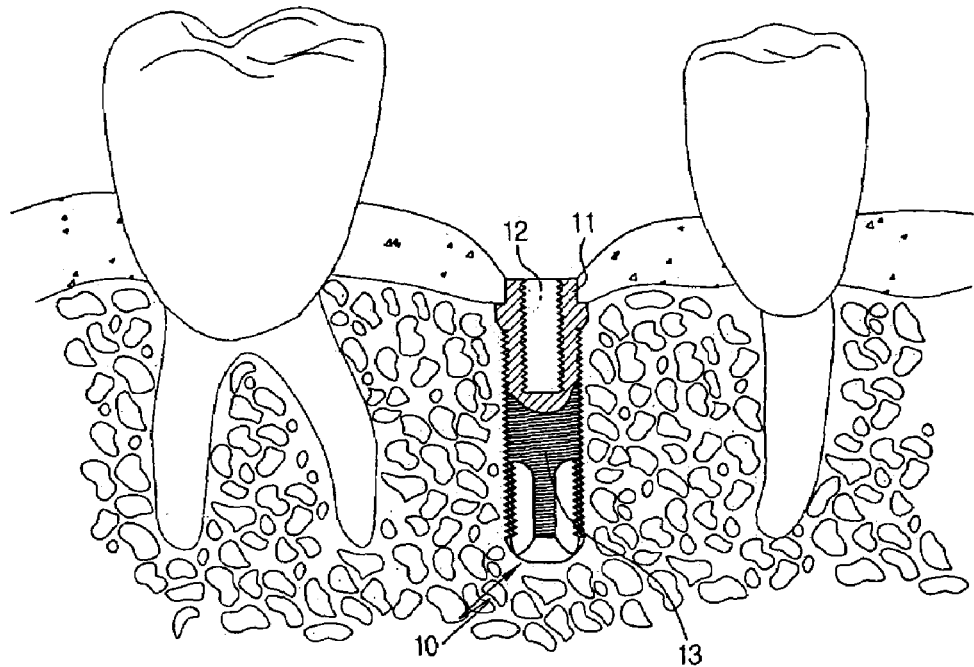
FIG. 12 shows an operation process of the dental implant according to the invention, in which a fixture fixed to a jawbone is shown.

Step 1: implanting fixture (refer to FIG. 12).

In this step, the fixture 10 is implanted into an edentulous site of a jawbone, and the implant screw 13 of the fixture 10 is firmly coupled to the jawbone in 6 months or so if the jawbone is in the upper jaw, whereas 4 months or so are required if it is in the lower jaw.

Figure 13:
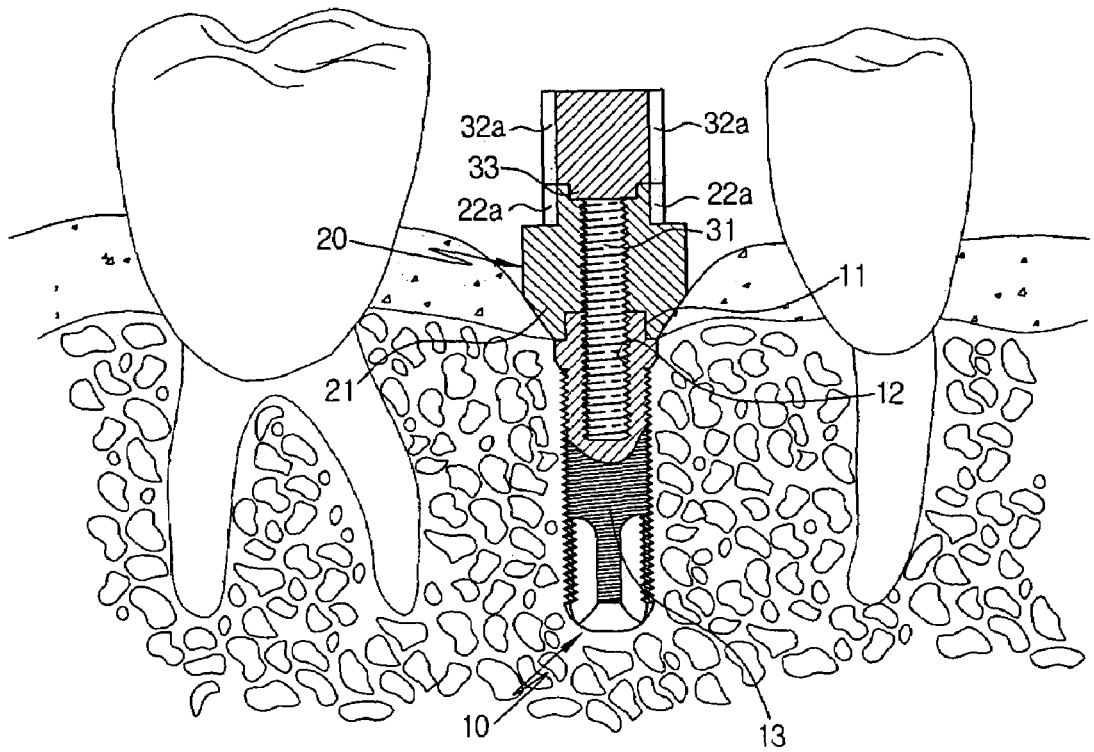
FIG. 13 shows the fixture coupled to an abutment and a solid screw in FIG. 12.

Step 2: coupling the abutment and the solid screw (refer to FIG. 13).

In this step, the abutment 20 is coupled to the abutment coupler 11 of the fixture 10 fixed to the jawbone, and the solid screw 30 passes through the abutment 20 and is fixed to the female screw thread 12 of the fixture 10.

At this point, the first and the second sleeve resting grooves 22*a*, 32*a* of the abutment 20 and the solid screw 30 are fixed to the fixture 10 in a communicated form.

Figure 14:
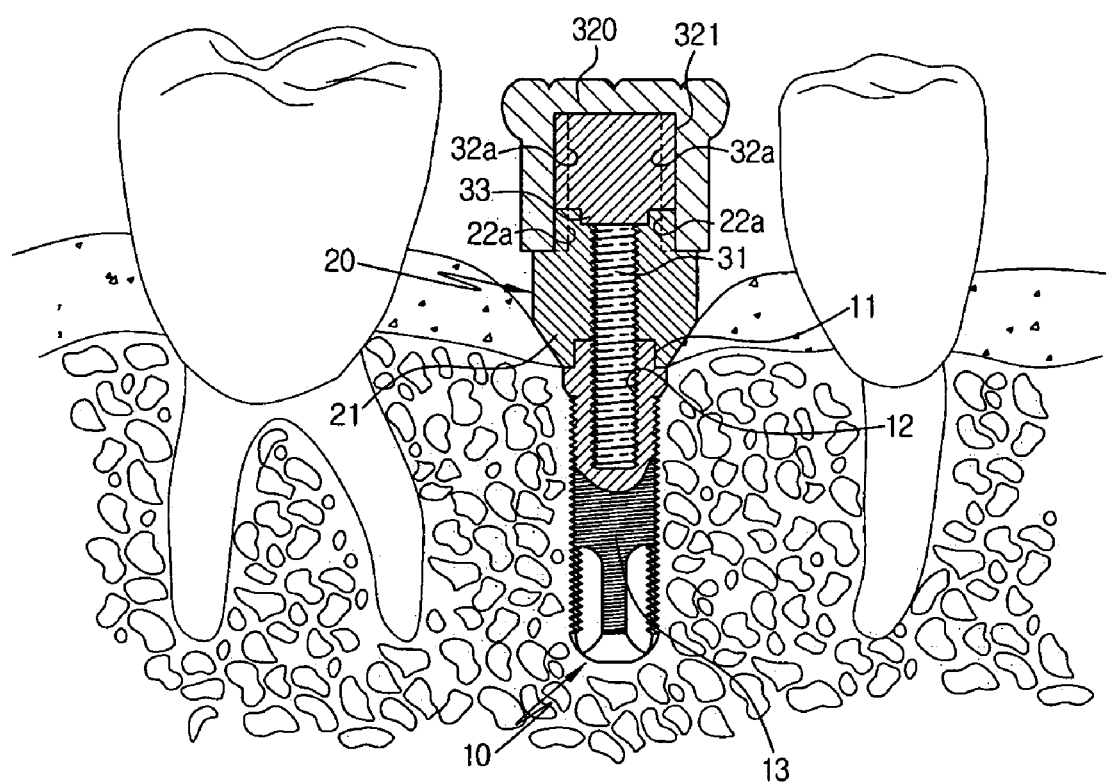
FIG. 14 shows an impression in FIG. 13 coupled with a cap.

Step 3: inserting the impression cap (refer to FIG. 14).

In this step, the impression cap 320 is inserted onto the upper portions of the abutment 20 and the solid screw 30, and the location of the crown is decided.

Figure 15:
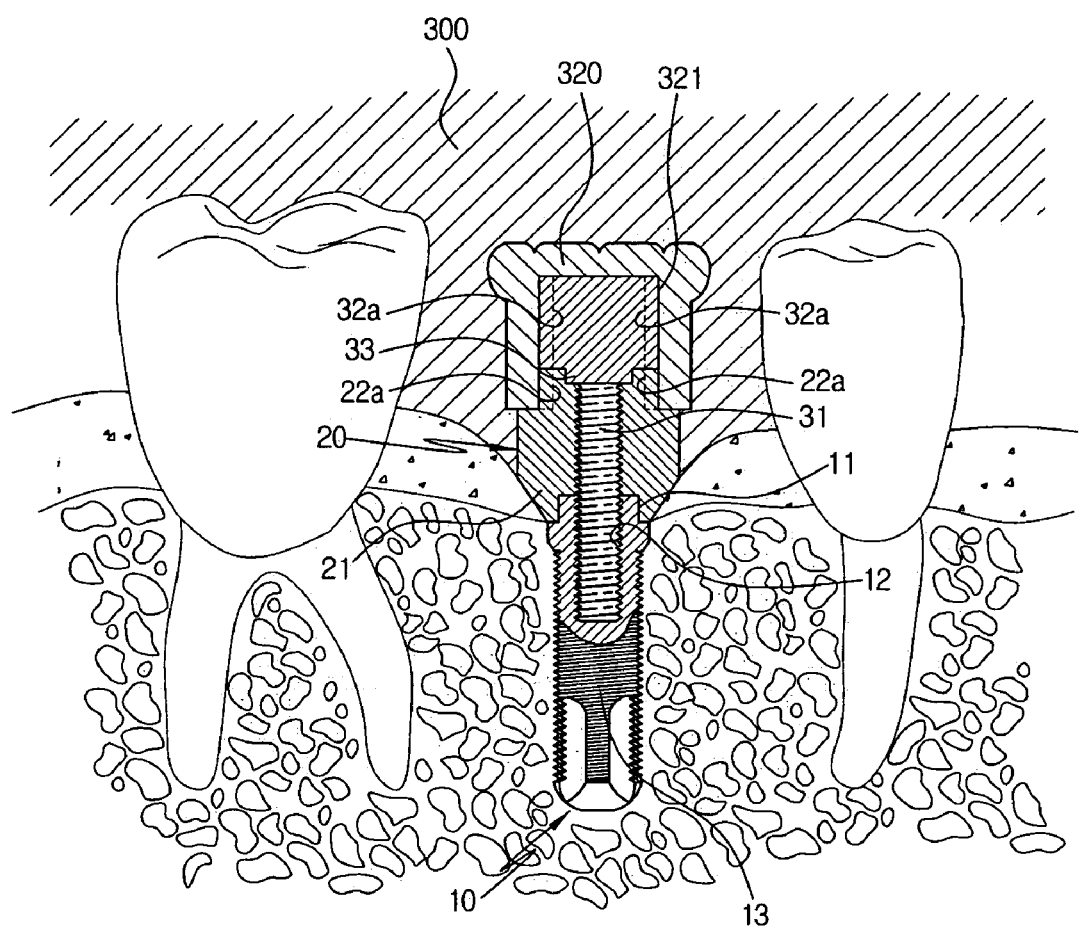
FIG. 15 shows the process of taking the impression in FIG. 14.
Figure 16:
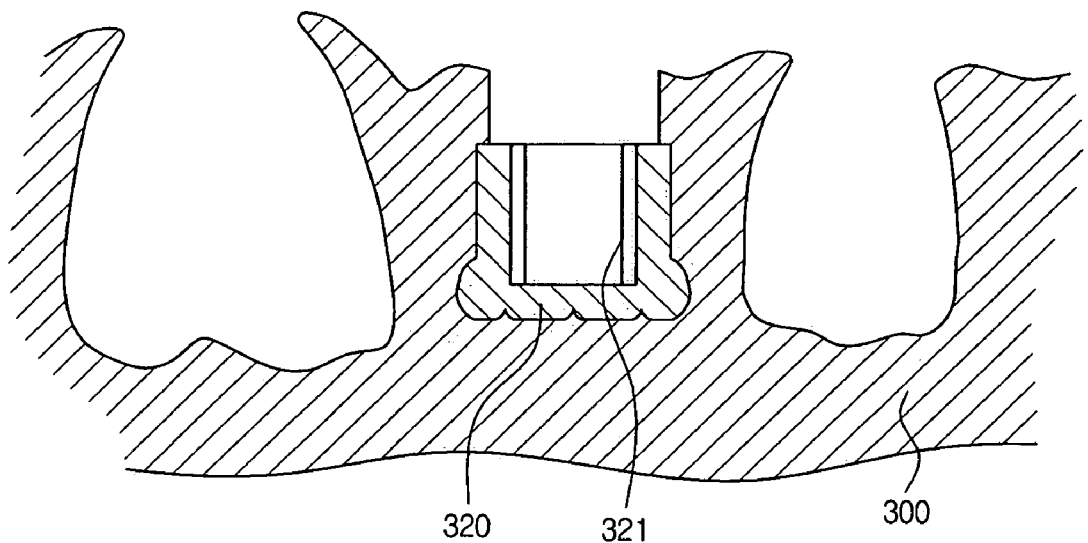
FIG. 16 shows the impression separated from the oral cavity, which is taken in FIG. 15.

Step 4: taking the impression (refer to FIGS. 15 and 16).

In this step, impression material is put on the impression tray (not shown) inside the oral cavity in which the impression cap 320 is coupled, and the impression 300 is taken, thereby obtaining the impression 300 so as to decide the locations of the abutment 20 and the solid screw 30 in the working model 310.

Figure 17:
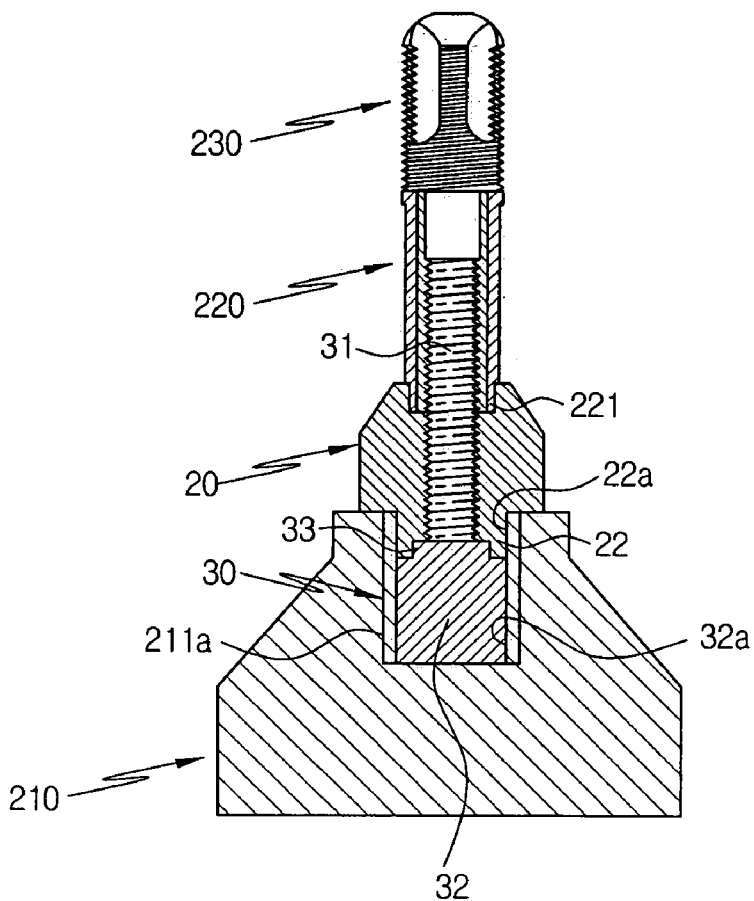
FIG. 17 shows the abutment and the solid screw coupled to the fixture of FIG. 13 being separated from the fixture and combined to the correction device.

Step 5: coupling the correction device which removes the rotational tolerance of the screw (refer to FIG. 17).

In this step, the abutment 20 and the solid screw 30 are separated from the fixture 10 fixed to the jawbone, and the dental analog body 220 and the analog screw 230 are assembled one after another. Then, the first and the second sleeve resting groves 22*a*, 32*a* of the abutment 20 and the solid screw 30 are coupled to the sleeve 211*a* formed at the receiving hole 211 of the jig 210.

At this point, with the coupler 221 of the dental analog body 220 being coupled to the abutment 20, the female screw 231 of the analog screw 230 is fixed to the coupling screw thread 31 of the solid screw 30, and the first and the second sleeve resting grooves 22*a*, 32*a* of the abutment 20 and the solid screw 30 are communicated, thereby removing the rotational tolerance.

Figure 18:
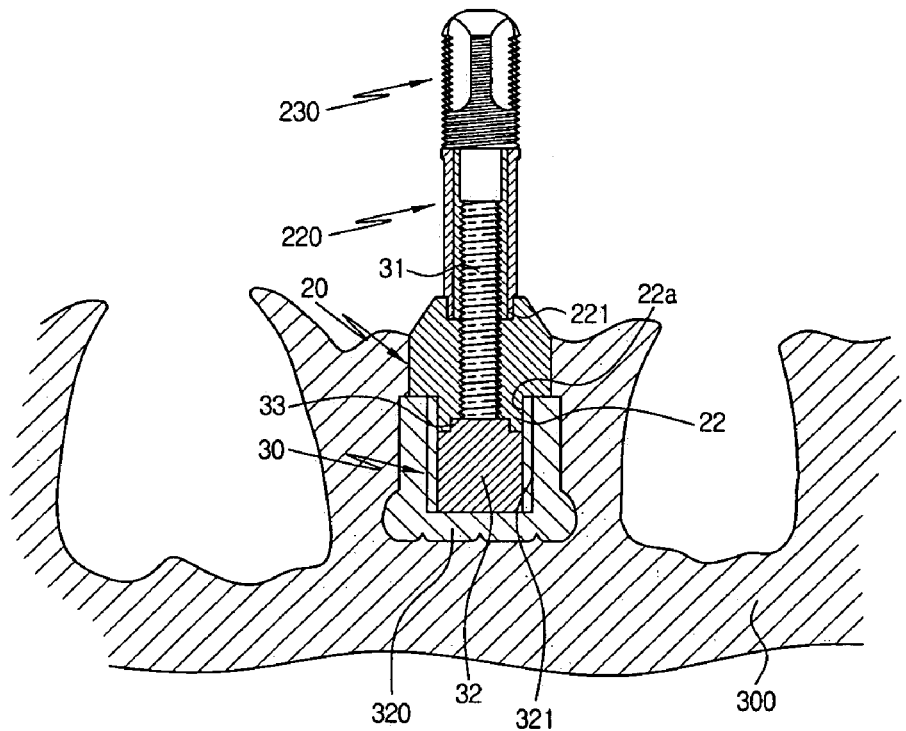
FIG. 18 shows the correction device corrected in FIG. 17 being coupled to the impression cap of FIG. 16.

Step 6: coupling the assembly of the correction device to the inside the impression cap of the impression (refer to FIG. 18).

In this step, the assembly A is separated from the jig 210 of the correction device and coupled to the impression cap 320 embedded in the impression 300.

At this point, the first and the second sleeve resting grooves 22*a*, 32*a* of the abutment 20 and the solid screw 30 in the assembly A are coupled to the sleeve 321 of the impression cap 320.

Figure 19:
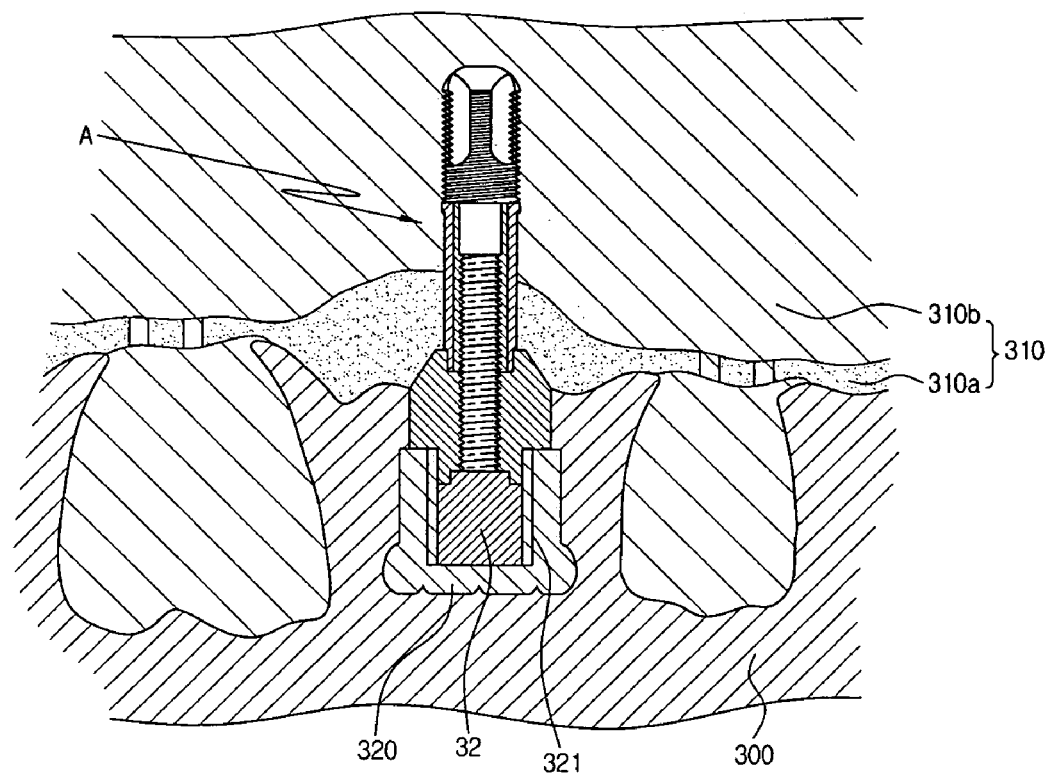
FIG. 19 shows the step of forming a working model by filling plaster in FIG. 18.
Figure 20:
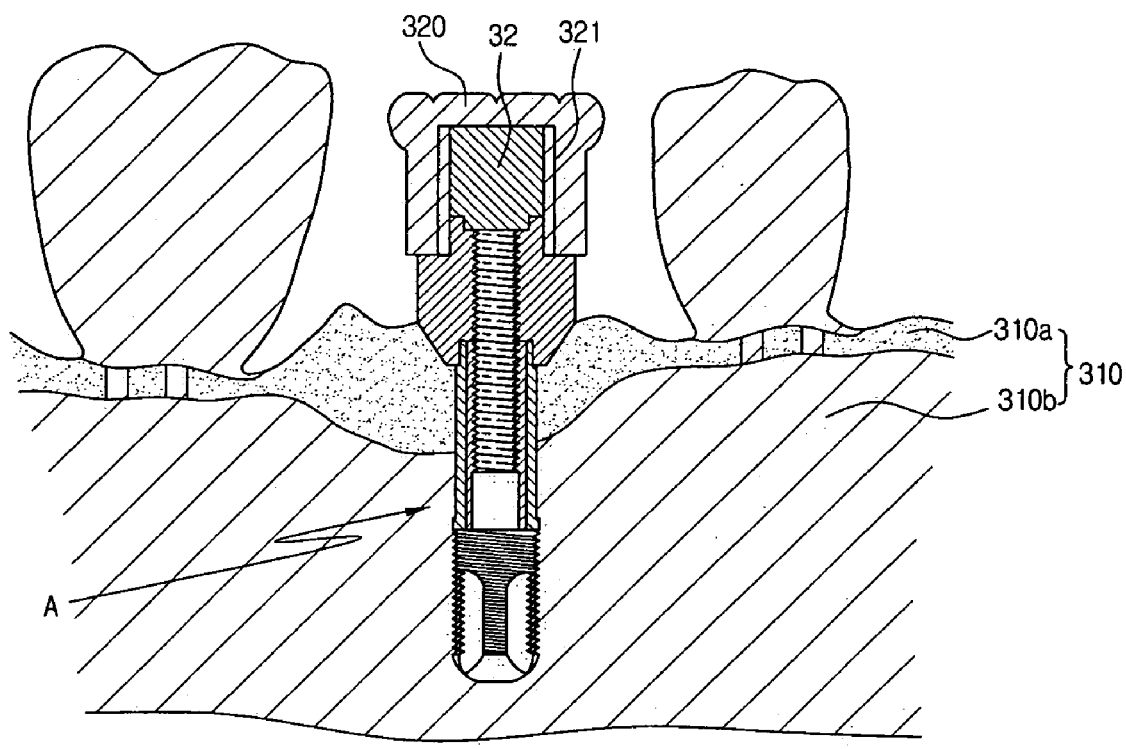
FIG. 20 shows the working model separated from the impression in FIG. 19.

Step 7: forming the working model (refer to FIGS. 19 and 20).

In this step, forming material 310*a* and plaster 310*b* are filled in the assembly A fixed to the impression cap 320 and then hardened, and the impression 300 is removed, thereby forming the working model 310.

That is, the working model 310 is formed of the same structure as the inside of the oral cavity.

Figure 21:
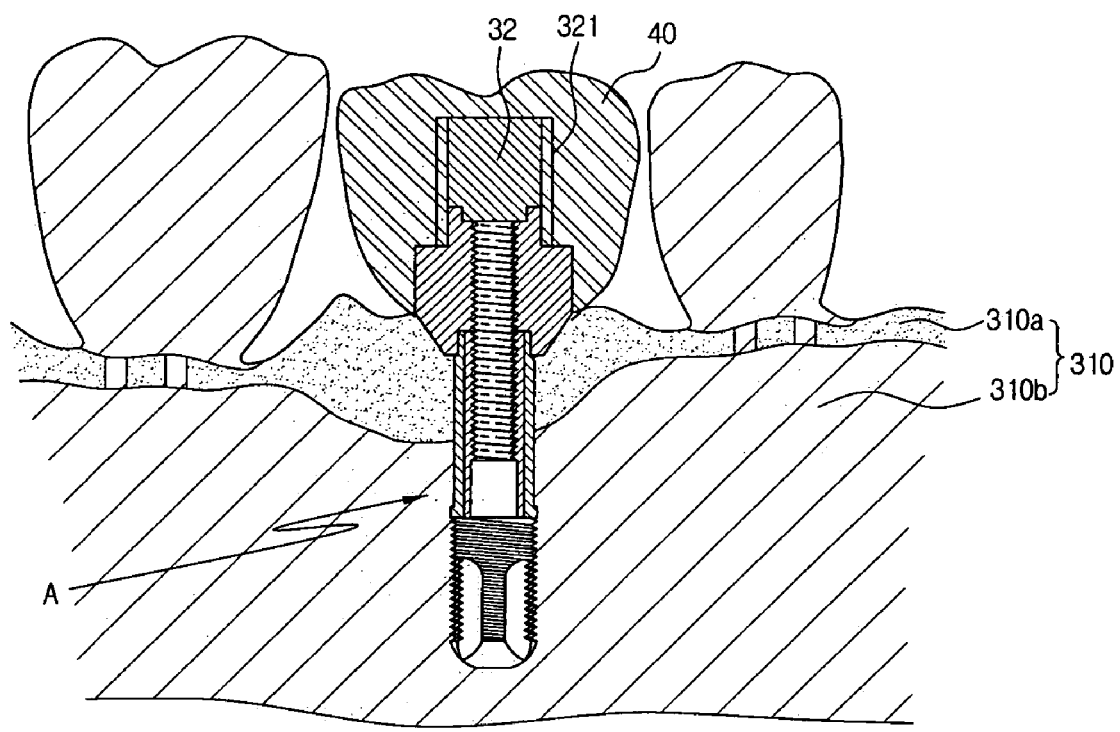
FIG. 21 shows the step of forming an artificial tooth crown at the working model of FIG. 20.

Step 8: forming the crown (refer to FIG. 21).

In this step, the crown 40 is coupled to the abutment 20 and the solid screw 30 which are on the working model 310, and the forming process is performed.

In addition, the inner sleeve projection 41 of the crown 40 is coupled to the first and the second sleeve resting grooves 22*a*, 32*a* of the abutment 20 and the solid screw 30.

Figure 22:
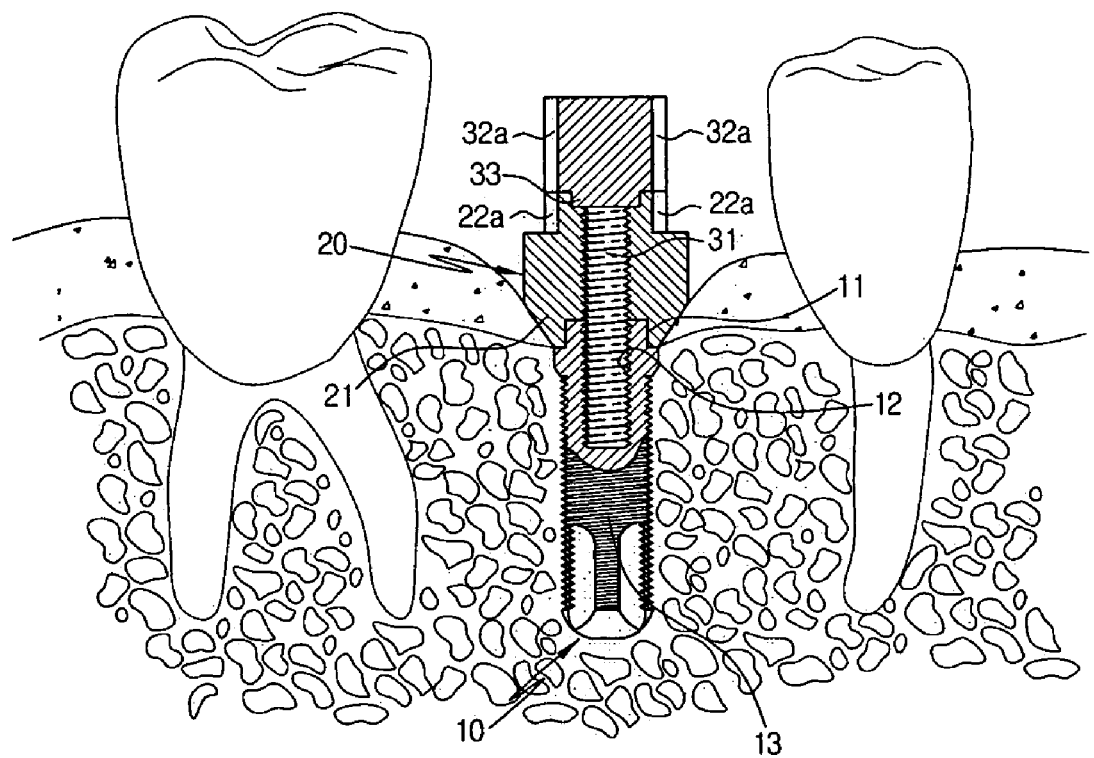
FIG. 22 shows the abutment and the solid screw on the working model in FIG. 20 being coupled to the fixture in the oral cavity.

Step 9: re-coupling the abutment and the solid screw to the fixture (refer to FIG. 22).

In this step, after separating the manufactured crown 40 from the working model 310, the abutment 20 and the solid screw 30 fixed to the working model 310 are separated and re-coupled to the fixture 10 implanted into the jawbone inside the oral cavity.

Figure 23:
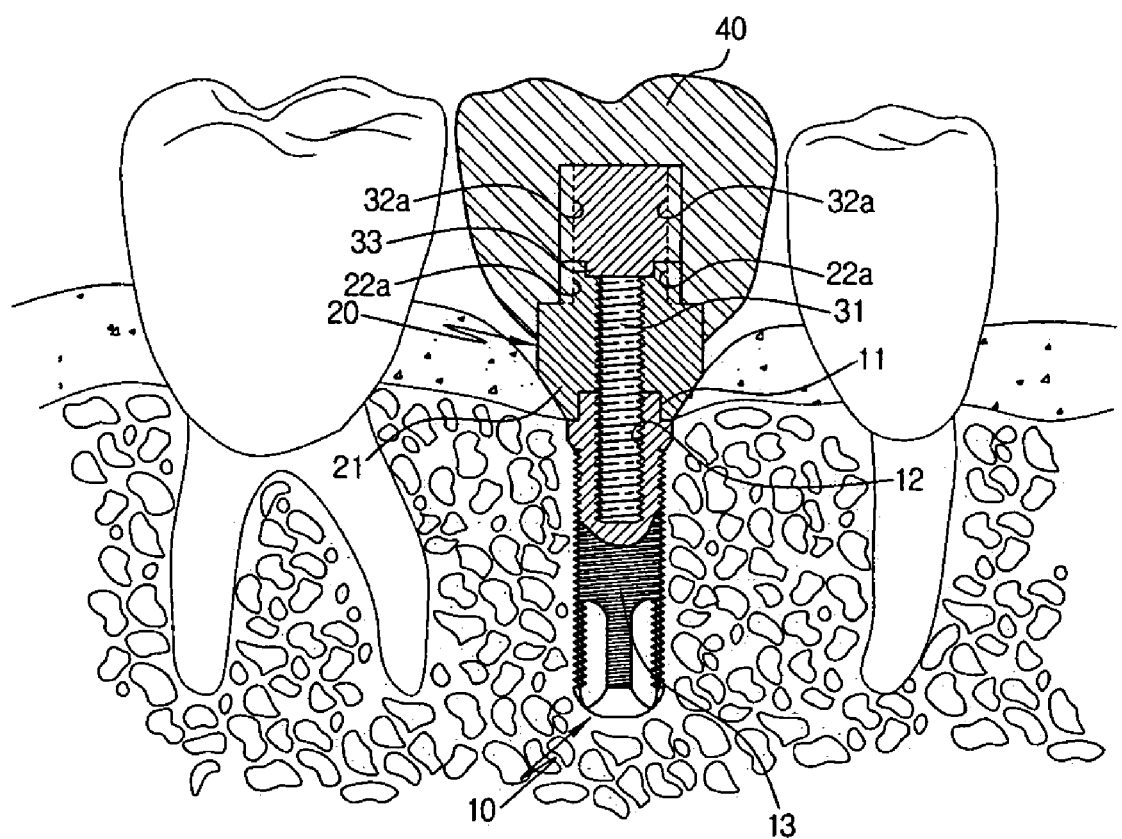
FIG. 23 shows the abutment of FIG. 22 covered with the crown.

Step 10: setting up the crown inside the oral cavity (refer to FIG. 23).

In this step, the crown 40 formed at the working model 310 is coupled to fixture 10 fixed to the abutment 20 and the solid screw 30 inside the oral cavity.

In addition, the sleeve projection 41 of the crown 40 is coupled to the first and the second sleeve resting grooves 22a, 32a of the abutment 20 and the solid screw 30.

That is, the crown 40 is accurately formed at the working model 310 and coupled inside the oral cavity, so that cement and the like is not required.

As described above in detail, in the dental implant device according to the invention, the sleeve of the crown is coupled to the sleeve resting grooves formed on the outer circumferential surfaces of the abutment and the solid screw, the abutment and the solid screw coupled to the fixture implanted into an edentulous site of a jawbone, so that a screw-loosening problem can be prevented.

In addition, due to the accuracy of the work, the crown can be mounted inside the oral cavity without using cement. It is simple to separate when removing the crown, therefore the maintenance becomes easy.

In addition, in the correction device used for the dental implant device of the invention, the exact location of the abutment and the solid screw inside the oral cavity can be transferred to the working model.

In addition, in the correction device used for the dental implant device of the invention, the dental analog body is assembled with the abutment, and then the coupling screw of the solid screw is coupled to the female screw of the analog screw, thereby removing the rotational tolerance of the screw.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A dental implant device comprising:
    an implant fixture provided with an abutment coupler at the upper portion of a commercialized fixture type, the abutment coupler having a female screw thread formed inside, and said fixture has a screw thread formed at the lower portion for implanting into the edentulous site of a jawbone;
    a separate abutment having at the lower portion thereof a first coupler and at the upper portion thereof a second coupler, the first coupler being coupled to the abutment coupler of said fixture, and said abutment being provided with a first sleeve resting groove on the outer circumferential surface of the second coupler;
    a solid screw formed at the lower portion with a coupling screw thread and at the upper portion with a head, the coupling screw passing through the abutment and said coupling screw thread being coupled to the said female screw thread of the fixture, the head having a second sleeve resting groove formed on the outer circumferential surface thereof, said first sleeve resting groove and said second sleeve resting groove being aligned; and
    a sleeve that is formed inside an artificial tooth and having a sleeve projection formed on the sleeve interior that is press-fittingly coupled to the first and the second sleeve resting grooves.

2. The device according to claim 1, wherein the first and the second sleeve resting grooves are formed in at least two pieces.

3. The device according to claim 1, wherein the abutment coupler of the fixture and the corresponding first coupler of the abutment are each formed to have a shape selected from the group consisting of a rectangular shape, a hexagonal shape, and an octagonal shape.

4. The device according to claim 1, wherein an intermediate step is formed between the head and coupling screw of the solid screw and is coupled to another step formed inside the second coupler of the abutment.

5. The device according to claim 1, wherein at least one of the height h and width w of the first and the second sleeve resting grooves are different in size.

* * * * *